United States Patent [19]

Lacko et al.

[11] Patent Number: 4,490,141
[45] Date of Patent: Dec. 25, 1984

[54] CATHETER STABILIZER AND METHOD OF SECURING SAME TO A PATIENT

[75] Inventors: Mark A. Lacko, Brooklyn; Malcolm J. Brooks; Douglas M. Spranger, both of New York, all of N.Y.; Peter P. Mitchell, Hoboken, N.J.

[73] Assignee: Becton Dickinson and Company, Paramus, N.J.

[21] Appl. No.: 404,991

[22] Filed: Aug. 4, 1982

[51] Int. Cl.³ ............................................. A61M 25/02
[52] U.S. Cl. .................................. 604/180; 128/133; 128/DIG. 26
[58] Field of Search ............... 128/133, DIG. 26; 604/179, 180

[56] References Cited

U.S. PATENT DOCUMENTS

| | | | |
|---|---|---|---|
| 2,821,194 | 1/1958 | Simmons | 604/180 |
| 3,918,446 | 11/1975 | Buttaravoli | 128/133 |
| 3,973,565 | 8/1976 | Steer | 604/180 |
| 4,059,105 | 11/1977 | Cutruzzula et al. | 604/133 |

Primary Examiner—Dalton L. Truluck
Attorney, Agent, or Firm—Richard J. Rodrick; Richard E. Brown

[57] ABSTRACT

A device for securing a catheter or like instrument to a patient comprises a first portion having an adhesive surface for securing that portion to the skin of a patient. A second portion is hingedly connected to the first portion and is adapted to fold thereover. The second portion has an adhesive surface to provide securement to the first portion when folded thereover. A slot and a hole are preferably associated with the first and second portions, respectively, for operably positioning the second portion around a catheter, which has been previously connected to the patient, so that the catheter extends through the plane formed by the second portion. This arrangement thereby facilitates the securement of the catheter in place on the patient.

A method of securing a previously connected catheter or like instrument to a patient includes securing a device substantially as described above to a patient.

15 Claims, 9 Drawing Figures

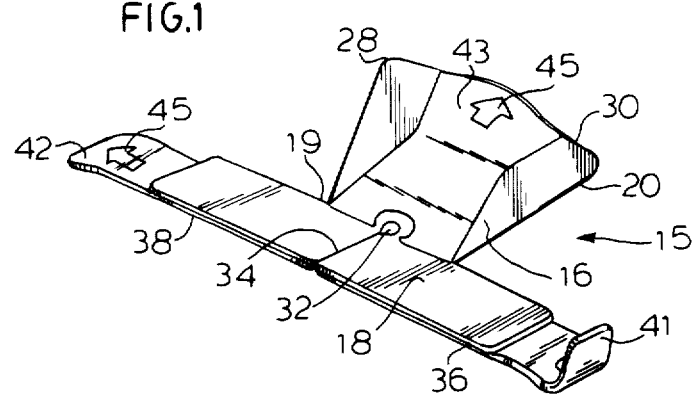
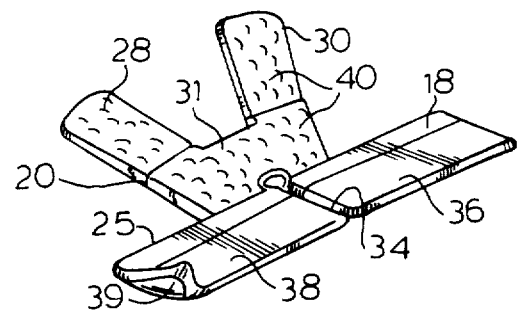
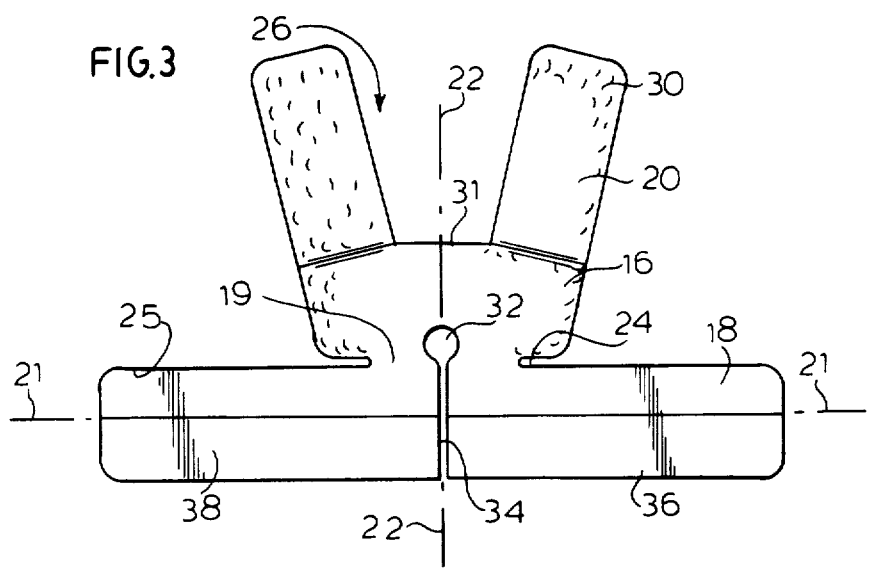

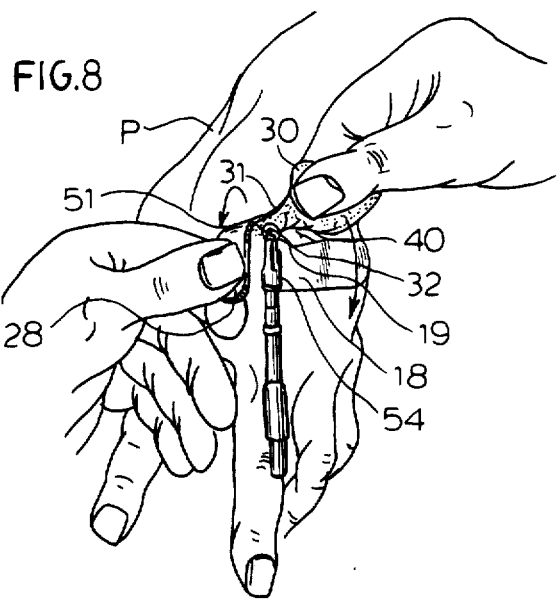
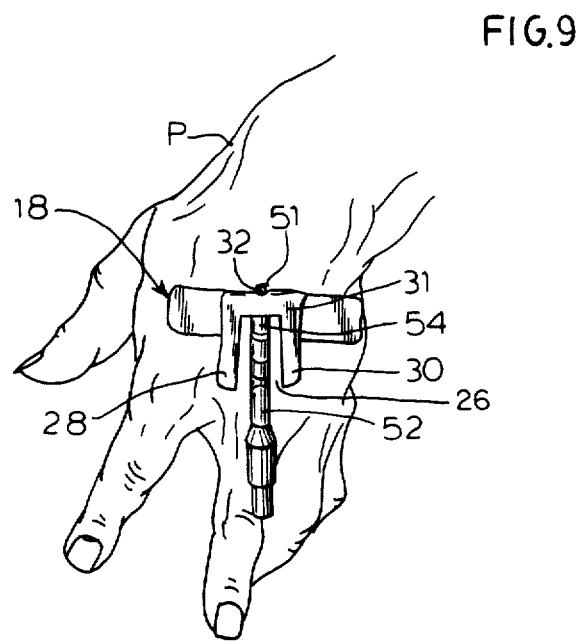

CATHETER STABILIZER AND METHOD OF SECURING SAME TO A PATIENT

BACKGROUND OF THE INVENTION

1. Field of the Invention

The present invention relates to a device for securing a catheter or like instrument to a patient and the method for same, and more particularly, concerns a securement device which, after applied, stabilizes the position of the catheter or like instrument in position on the patient.

2. Description of the Prior Art

When connections are made to a patient, such as for intravenous feeding or angiography, the catheter connection is usually taped to the patient in order to securely maintain it in position. Many hospitals use a conventional "chevron" taping technique at the site of the catheter connection. This chevron technique takes time to apply, and, of course, varies in its final configuration since each one is individually applied. Techniques for improving the securement of the catheter to the patient have been sought after and proposed.

For example, U.S. Pat. No. 4,059,105 describes a device for securing a cannula to a patient which includes a one piece lamina foldable over the cannula which is inserted in the patient. This foldable device is also illustrated in U.S. Pat. No. 243,477. While the device described in the above patents is meant to provide a technique for securing a cannula in place, there are still some problems inherent in this patented device. In particular, the securing device completely covers the catheter connection. In order to view the insertion site, the wider portion of the patented device must be raised. This also would cause inconvenience if a tubing change were to be required at the catheter site.

A similar foldable securing device which covers the insertion site is described in U.S. Pat. No. 3,973,565.

Another securement device for an intravenous catheter is described in U.S. Pat. No. 3,918,446. In this patent, the bottom pad includes at least one slit extending from an edge inwardly of the bottom pad and terminates in an enlarged perforation serving as a medicament well for ointment. A flap is then applied over the infusion needle to sandwich the same in between the flap and the bottom pad. This patent requires a somewhat complex arrangement and structure in order to be operable.

It can be seen that improvements in the field of securing catheters and like devices to a patient are still being sought. It is to this end that the present invention is directed.

SUMMARY OF THE INVENTION

The device of the present invention for securing a catheter or like instrument to a patient comprises a first portion having an adhesive surface for securing it to the skin of a patient. A second portion is hingedly connected to the first portion and is adapted to fold over the first portion. The second portion also has an adhesive surface to provide securement to the first portion when folded thereover. Means is associated with the first and second portions for operably positioning the second portion around a catheter or like instrument, which has been previously connected to the patient, so that the catheter or like instrument extends through the plane formed by the second portion. This facilitates the securement of the catheter or like instrument in place on the patient.

In a preferred embodiment of this aspect of the invention, the second portion has a hole therethrough adjacent the hinged connected for surrounding the catheter. This second portion also includes a cut-out area forming two wing segments tapering inwardly in converging fashion toward the first portion. A slot extends across the first portion and communicates with the hole thereby dividing this first portion into two separable segments for positioning around the catheter and facilitating the securement of the first portion to the skin of a patient.

In another aspect of the present invention, a method of securing a previously connected catheter or like instrument to a patient comprises separating two separable segments of an anchoring portion of a securing device. The segments each have an adhesive surface thereon. The method further includes placing a stabilizing portion of the device around the catheter or like instrument, and then placing the separated segments under the catheter or like instrument. The stabilizing portion also has an adhesive surface thereon. Next, the edges of the segments are aligned in substantial juxtaposition with each other under the catheter or like instrument. Following this, the method includes securing the adhesive surfaces of the segments to the skin of the patient, and then folding the stabilizing portion over the catheter or like instruments and the segments so that the adhesive surface of the stabilizing portion faces toward the patient. The adhesive surface of the stabilizing portion is then secured over the catheter or like instrument.

In accordance with the principles of the present invention, the stabilizer device herein may be used to replace conventional "chevron" taping techniques commonly employed in hospitals. The present invention is intended to minimize lateral, rotational and axial (pistoning) movements of the catheter at the site where it is connected to the patient. On the other hand, the present invention allows access for site inspection at the puncture site and catheter tip. In addition, the present invention provides cushioning of the catheter hub where it would normally contact the patient if conventional chevron taping techniques were employed. Moreover, the present invention facilitates routine tubing changes without disturbing the position of the catheter or its connecting site. Another feature is the minimization or elimination of contamination by touch in order to maintain a sterile technique. The stabilizer device of the present invention is fast and simple to apply.

BRIEF DESCRIPTION OF THE DRAWINGS

FIG. 1 is a perspective view of the preferred stabilizer device of the present invention, illustrated with removable protective sheets;

FIG. 2 is a perspective view of the preferred stabilizer device of the present invention as illustrated with the protective sheets removed;

FIG. 3 is an enlarged top plan view of the stabilizer device of FIG. 2; and

FIGS. 4–9 illustrate the sequential steps in applying the stabilizer device of FIG. 1 and securing and stabilizing a catheter in place on the hand of a patient.

DETAILED DESCRIPTION

Figure 4:
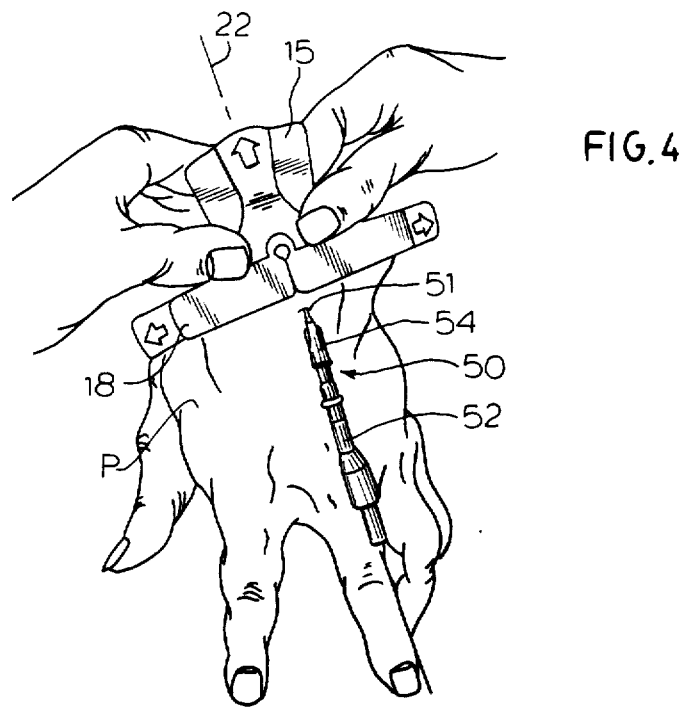

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiments illustrated. The scope of the invention will be measured by the appended claims and their equivalents.

Adverting to the drawings, and FIGS. 1–3 in particular, there is illustrated the preferred stabilizer device 15 of the present invention. The main component of stabilizer device 15 is a body member 16 which may be made in a unitary, integrally formed structure. Comprising body member 16 is an anchoring portion 18, a hinge 19 and a stabilizing portion 20.

Turning to anchoring portion 18, it is preferably formed having an elongate transverse dimension, or elongated rectangular shape, as more clearly seen in FIG. 3. For purposes of directional reference, the transverse direction is that direction taken along center line 21 as seen in FIG. 3. As will be pointed out hereafter, anchoring portion 18 is generally adhered to the patient transverse to the orientation of the axis of the catheter. Center line 22 as seen in FIG. 3 shall hereinafter be referred to as the axial direction. Although the anchoring portion is being described herein as rectangularly shaped, it is understood that the invention is not restricted to this shape, and that other shapes or configurations may be utilized.

Stabilizing portion 20 is connected to anchoring portion 18 by virtue of an intermediate portion which serves as hinge 19. In order to facilitate folding of the stabilizing portion over the anchoring portion, hinge 19 preferably includes an undercut area 24 so that its transverse dimension is shorter than both of the stabilizing and anchoring portions. In its broadest application, hinge 19 may be no more than an area readily foldable so that stabilizing portion 20 can be folded over anchoring portion 18.

Stabilizing portion 20 is connected by hinge 19 along one of the elongate sides 25 of the anchoring portion. It is preferred that the stabilizing portion also be centered along axial center line 22. In its preferred form, stabilizing portion 20 is much shorter in the transverse direction than the anchoring portion. Stabilizing portion 20 is desirably formed in a V-like configuration with a cut-out area 26 forming two wing segments 28 and 30, respectively. Cut-out area 26 is, however, truncated so that a body portion 31 remains between wing segments 28 and 30. In the V-like configuration, wing segments 28 and 30 taper inwardly in converging fashion toward anchoring portion 18. This configuration contributes to effectively securing the catheter in place on the patient. Also, wing segments 28 and 30 are preferably made somewhat long so that when the stabilizing portion is folded over the anchoring portion there will be some overlap onto the skin of the patient as is illustrated in FIG. 9 and which will be described hereinafter.

As seen most clearly in FIGS. 1–3, body portion 31 of the stabilizing portion has a hole 32 therethrough. This hole, in the embodiment being described, is along the axial center line 22 and is adjacent hinge 19. Part of hole 32 may lie in the hinged area so as to be as close as possible to the anchoring portion. Hole 32 is generally sized so as to fit around the narrow, tapered end portion of a typical catheter hub, such as at the interface between catheter hub and needle. Of course, the diameter of the hole may differ in stabilizer devices used for different purposes; however, the hole should not be so large that the main body of the catheter hub could slide completely therethrough. Since most catheter hubs are tapered, the size of the hole can be selected so as to prevent this from occurring.

Extending across the shorter length of anchoring portion 18, and preferably along center line 22, is a slot 34. This slot also extends through hinge 19 terminating at and communicating with hole 32. The effect of slot 34 is to divide anchoring portion 18 into two separable segments 36 and 38, respectively. Even though slot 34 communicates with hole 32, each respective separable segment is still connected to the stabilizing portion through the hinged connection. It is appreciated that the flexible nature of the body member material will allow separable segments 36 and 38 to be spread apart from each other along the slot.

Referring particularly to FIG. 2, anchoring portion 18 includes an adhesive material 39 on its lower surface. Both of the separable segments include this adhesive material. The lower surface of the anchoring portion is that surface which makes contact with the skin of the patient. On the other hand, stabilizing portion 20 has an adhesive material 40 on its upper surface. When stabilizing portion 20 is folded over anchoring portion 18, adhesive surface 40 will contribute to securing the stabilizer device and the catheter in place. While FIG. 2 shows adhesive material 40 on the entire upper surface of the stabilizing portion (except for hole 32), the entire area need not be adhesively covered. For example, portions of wing segments 28 and 30 may be left adhesive-free so that they may be conveniently grasped when it is time to lift this stabilizer device away from the patient after use.

Removable protective sheets 41, 42 and 43 cover the adhesive areas on separable segments 36 and 38 and stabilizing portion 20, respectively. Protective sheets 41 and 42 are individually removable from the two separable segments of the anchoring portion. As seen more clearly in FIG. 1, protective sheets 41 and 42 extend beyond the respective lateral ends of the anchoring portion to facilitate grasping for their removal. In addition, arrows 45 may be provided to indicate to the user that direction toward which the protective sheets should be pulled for removal.

While many different materials may be utilized for the body member of the stabilizer device herein, it is preferred that the material be thin and flexible, but yet sufficiently strong to provide the stabilizer features herein described. One such material which may be used is nonwoven synthetic felt. The adhesive coating for the previously described surfaces may be any of the well-known and utilized adhesive coating techniques commonly found on bandages and the like. The removable protective sheet may be paper or the like.

Figure 5:
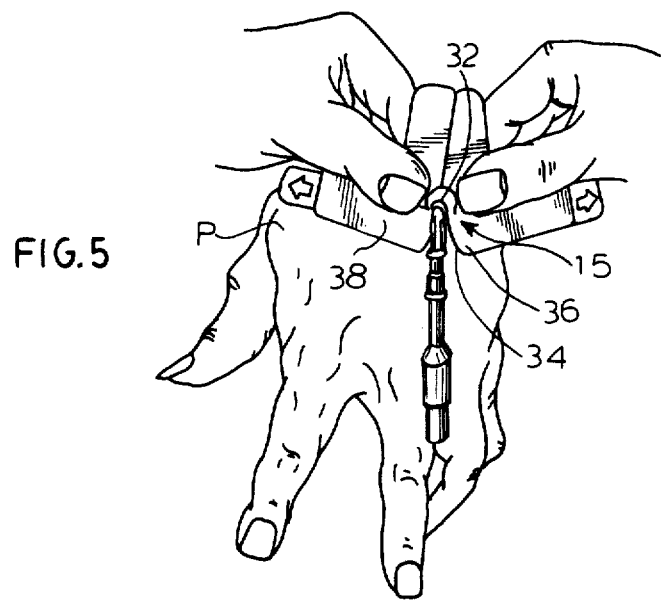
Figure 6:
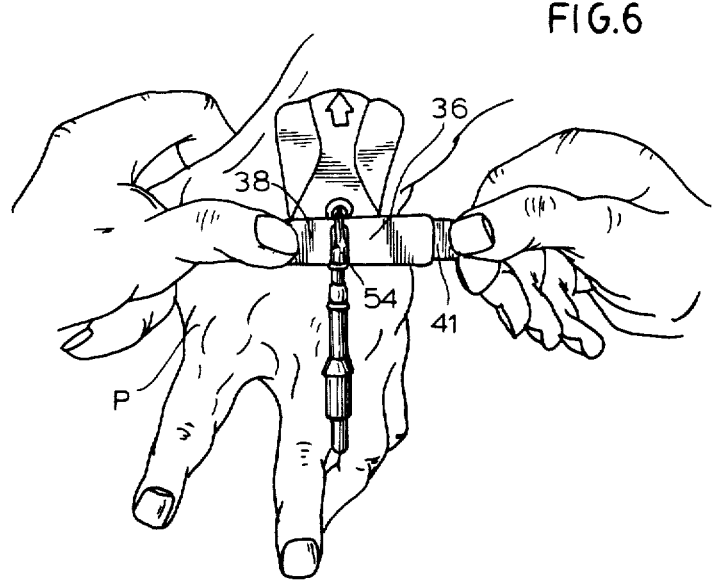

FIGS. 4–9 illustrate the sequential steps of applying stabilizer device 15 to the patient and securing a previously inserted catheter device in position on the patient. Turning first to FIG. 4, catheter device 50 is illustrated as being connected to the Patient P. While a catheter is described herein in conjunction with the present invention, it is understood that other instruments or devices which require a fixed position with respect to the patient may be secured by use of the present stabilizer device. A needle 51 has penetrated patient P's skin, while tubing 52 is connected to catheter hub 54. The attendant holds stabilizer device 15 and aligns same so that center line 22 is axially aligned with the inserted needle 51. Anchoring portion 18 is thus ready to be positioned transversely across the catheter arrangement. Once oriented, separable segments 36 and 38 are separated by the attendant as seen in FIG. 5. Slot 34 is opened up and placed over catheter hub 54 so that the tip of the catheter hub at the interface with needle 51 is positioned in hole 32. Once hole 32 surrounds the tip of the catheter hub, separated segments 36 and 38 are then placed under the catheter hub. The interior edges of separable segments 36 and 38 are brought together under the catheter hub so as to be in substantial juxtaposition with each other in abutting fashion. At this stage, the catheter extends through hole 32 and thus through the plane formed by the stabilizing portion.

Figure 7:
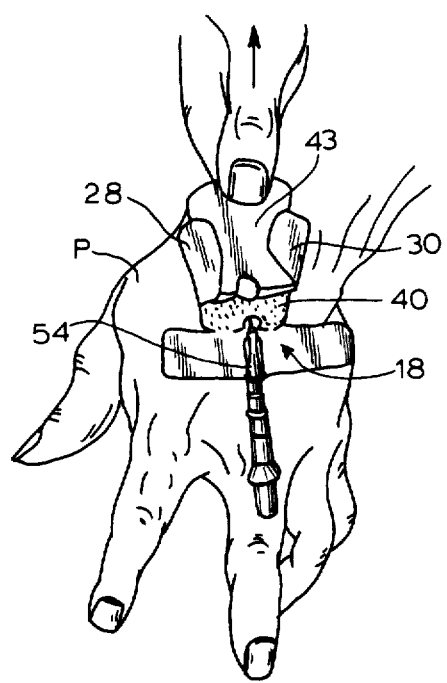

Once this arrangement has been completed, the attendant holds separable segment 38 with thumb pressure while pulling outwardly on removeable protective sheet 41. Removal of this protective sheet will expose the adhesive material on the lower surface of segment 36. Firm pressing on segment 36 will secure it to the hand of the patient. Segment 38 is also adhered to the patient in likewise fashion, abutting segment 36 to thereby provide a cushion for the catheter hub to increase patient comfort. Once the entire anchoring portion 18 has been secured to the skin of the patient, the attendant then pulls upwardly on removeable protective sheet 43 as illustrated in FIG. 7. Adhesive material 40 is then exposed, as well as wing segments 28 and 30. In FIG. 8, the attendant is shown folding wing segments 28 and 30 at the hinge area 19 over anchoring portion 18. It is noted that during the folding procedure, needle 51 remains inserted in patient P through hole 32. Each wing segment is folded against the upper surface of anchoring portion 18 so that adhesive surface 40 contacts same. This effectively secures the stabilizing portion to the anchoring portion. It is preferred that each wing segment be secured to the anchoring portion on opposite sides of catheter hub 54 in substantially axial alignment therewith. In the embodiment being described, wing segments 28 and 30 are sufficiently long to also extend onto the skin of the patient. Additional adhesive material at the ends of these wing segments permits them to be adhesively secured to the skin of the patient. On the other hand, it may be desirable to omit adhesive material at the ends of the wing segments so that they can be readily lifted off the skin of the patient when it is time to remove the stabilizer device from the patient. At the same time the wing segments are folded, body portion 31 is folded directly over catheter hub 54, as more clearly seen in FIG. 9. This serves to effectively hold the catheter hub in a fixed position during its use. However, due to the cut-out area between wing segments 28 and 30, it can be seen that the connection site between tubing 52 and catheter hub 54 is accessible. This arrangement allows routine tubing changes without the necessity of disturbing the catheter position. As also seen in FIG. 9, with the stabilizing portion folded at hinge 19 over the anchoring portion, the puncture site of needle 51, as well as the tip of catheter hub 54, are viewable by the attendant. In addition, with the anchoring portion of the stabilizer device herein being positioned under the catheter hub, a cushioning effect is provided so that the catheter need not come in direct contact with the skin of the patient. Once the stabilizer device is completely secured in position, lateral, rotational and axial (pistoning) movements are minimized or prevented.

Thus, the present invention provides a catheter stabilizer and method of securing same to a patient which is disposable, fast and straightforward to apply. It provides a number of advantages over the prior art in its main function of securing and stabilizing a catheter or like instrument in position on the patient.

What is claimed is:

1. A stabilizer device for securing a catheter or like instrument to a patient comprising:
   an anchoring portion having an adhesive on a lower surface thereof for securing the same to the skin of a patient; and
   a stabilizing portion hingedly connected to said anchoring portion adapted to fold over said anchoring portion, said stabilizing portion having an adhesive on an upper surface for securing the stabilizing portion to the upper surface of said anchoring portion when folded thereover, said stabilizing portion having a hole therethrough adjacent said hinged connection for surrounding a catheter or like instrument which is connected to said patient, said anchoring portion having a slot thereacross communicating with said hole thereby dividing said anchoring portion into two separable segments for positioning around said catheter or like instrument and facilitating the securement of said anchoring portion to the patient.

2. The device of claim 1 wherein said anchoring portion is substantially longer in its transverse dimension than its axial dimension.

3. The device of claim 2 wherein said anchoring portion is substantially longer than the stabilizing portion in their respective transverse dimensions.

4. The device of claim 3 wherein said anchoring and said stabilizing portions are connected to each other by an intermediate portion having a shorter transverse dimension than both of said anchoring and stabilizing portions thereby serving as a hinge.

5. The device of claim 1 wherein said stabilizing portion includes a cut-out area forming two wing segments.

6. The device of claim 5 wherein said wing segments are formed to taper inwardly in converging fashion toward said anchoring portion.

7. The device of claims 5 or 6 wherein said wing segments are sufficiently long to adhere to the upper surface of said anchoring portion and the skin of the patient when folded over said anchoring portion.

8. The device of claim 1 wherein the adhesive surfaces of said anchoring and stabilizing portions are covered by removable protective sheets.

9. The device of claim 8 wherein there are individually removable protective sheets covering the adhesive surfaces of the two separable segments of said anchoring portion.

10. The device of claim 9 wherein the protective sheets for said two separable segments each extend beyond their respective lateral ends of the anchoring portion to facilitate grasping for their removal.

11. A device for securing a catheter or like instrument to a patient comprising:
   a first portion having an adhesive surface for securing same to the skin of a patient;
   a second portion hingedly connected to said first portion adapted to fold over said first portion and having an adhesive surface to provide securement to said first portion when so folded over;
   means associated with said first portion for operably positioning said first portion under a catheter or like instrument which has been previously connected to the patient; and
   means associated with said second portion communicating with said means associated with said first portion for operably positioning said catheter or like instrument in said second portion whereby said catheter or like instrument extends through the planes formed by said first and second portions to thereby facilitate the securement of said catheter or like instrument in place on said patient.

12. A stabilizer device for securing a catheter or like instrument to a patient comprising:

an anchoring portion having an elongate transverse dimension and an adhesive on a lower surface thereof for securing the same directly to the skin of a patient;

a stabilizing portion connected by a hinge to said anchoring portion along one of the elongate sides of said anchoring portion and having an adhesive on an upper surface for securing the stabilizing portion to the upper surface of said anchoring portion when folded thereover, said stabilizing portion having a hole therethrough adjacent said hinge for surrounding a catheter or like instrument which is connected to said patient, said stabilizing portion including a cut-out area forming two wing segments tapering inwardly in converging fashion toward said anchoring portion, said anchoring portion including a slot extending across the shorter length thereof and communicating with said hole thereby dividing said anchoring portion into two separable segments for positioning around said catheter or like instrument and facilitating the securement of said anchoring portion to the patient; and removable protective sheets covering the adhesive surfaces of said anchoring and stabilizing portions.

13. A method of securing a previously connected catheter or like instrument to a patient comprising:

separating two separable segments of an anchoring portion of a securing device, said segments each having an adhesive surface thereon;

placing a stabilizing portion connected by a hinge to said anchoring portion of said device around said catheter or like instrument, said stabilizing portion having an adhesive surface thereon, by maneuvering said separated segments and said hinge past opposite sides of said catheter or like instrument; whereby said catheter is located in said stabilizing portion;

placing said separated segments under said catheter or like instrument;

aligning the edges of said segments in substantial juxtaposition with each other under the catheter or like instrument;

securing the adhesive surfaces of said segments to the skin of the patient;

folding said stabilizing portion over said catheter or like instrument and said segments so that the adhesive surface of said stabilizing portion faces toward the patient; and securing the adhesive surface of said stabilizing portion over said catheter or like instrument.

14. The method of claim 13 wherein said device includes removable protective sheets covering the adhesive surfaces of said segments, the method including the step of removing said protective sheets after the separated segments have been placed under the catheter or like instrument.

15. The method of claims 13 or 14 wherein the device includes a removable protective sheet covering the adhesive surface of said stabilizing portion, the method including the step of removing the protective sheet from said stabilizing portion after the adhesive surfaces of said segments have been secured to the skin of the patient.

* * * * *